United States Patent [19]

Schulte-Elte

[11] Patent Number: 4,588,849

[45] Date of Patent: May 13, 1986

[54] PROCESS FOR THE PREPARATION OF AN ISOMERIC MIXTURE OF 1-(2,6,6-TRIMETHYLCYCLOHEXYL)-HEXAN-3-OL

[75] Inventor: Karl-Heinrich Schulte-Elte, Onex, Switzerland

[73] Assignee: Firmenich SA, Geneva, Switzerland

[21] Appl. No.: 584,500

[22] Filed: Feb. 28, 1984

[30] Foreign Application Priority Data

Mar. 11, 1983 [CH] Switzerland ................ 1340/83

[51] Int. Cl.[4] .............................................. C07C 35/08
[52] U.S. Cl. ..................................... 568/834; 568/822; 568/824; 252/522 R
[58] Field of Search ................ 568/834, 824, 822

[56] References Cited

U.S. PATENT DOCUMENTS

| | | | |
|---|---|---|---|
| 4,000,198 | 12/1976 | Rosenberger | 568/824 |
| 4,045,476 | 8/1977 | Rosenberger | 568/824 |
| 4,088,681 | 5/1978 | Bausmann et al. | 568/828 |
| 4,147,886 | 4/1979 | Wiederkher | 568/824 |
| 4,252,986 | 2/1981 | Klein et al. | 252/822 |
| 4,311,860 | 1/1982 | Krasnobejew | 568/824 |
| 4,313,855 | 2/1982 | Klein et al. | 252/522 R |
| 4,324,704 | 4/1982 | Trenkle et al. | 568/824 |

FOREIGN PATENT DOCUMENTS

| | | | |
|---|---|---|---|
| 2455761 | 6/1976 | Fed. Rep. of Germany | 568/824 |
| 2558806 | 7/1977 | Fed. Rep. of Germany | 568/824 |
| 2807584 | 2/1978 | Fed. Rep. of Germany | 568/824 |
| 2418214 | 9/1979 | France | 568/824 |

OTHER PUBLICATIONS

Helvetica Chimica Acta, 56, Paper No. 147, pp. 1503–1513 (1973).

*Primary Examiner*—Werren B. Lone
*Attorney, Agent, or Firm*—Pennie & Edmonds

[57] ABSTRACT

Process for the preparation of an isomeric mixture of cis- and trans-1-(2,6,6-trimethylcyclohexyl)-hexan-3-ol according to a three-step pathway starting from trimethylcyclohexanone.

4 Claims, No Drawings

PROCESS FOR THE PREPARATION OF AN ISOMERIC MIXTURE OF 1-(2,6,6-TRIMETHYLCYCLOHEXYL)-HEXAN-3-OL

BRIEF SUMMARY OF THE INVENTION

The instant invention relates to a process for the preparation of a composition containing a predominant amount, but not less than about 60% by weight, of trans-1-(2,6,6-trimethylcyclohexyl)-hexan-3-ol and a definite amount, but not more than about 40% by weight, of cis-1-(2,6,6-trimethylcyclohexyl)-hexan-3-ol, which process comprises the following sequential steps:

a. the addition of hex-1-yn-3-ol to 2,6,6-trimethylcyclohexanone to give 1-(1-hydroxy-2,6,6-trimethylcyclohexyl)-hex-1-yn-3-ol;

b. the reduction of said hexynol by means of an alkali metal aluminohydride to give an allenic carbinol of formula

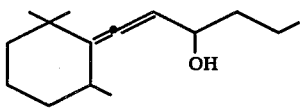

(II)

c. the catalytic hydrogenation of said carbinol at a pressure higher than the atmospheric pressure and in the presence of Raney-nickel and copper chromite, or, alternatively, c'. the catalytic hydrogenation of said carbinol at room temperature and atmospheric pressure in the presence of PtO$_2$.

This invention relates further to the utilization of the thus prepared composition as perfume ingredient.

The invention relates also to allenic carbinol intermediate of formula (II) and to 1-(1-hydroxy-2,6,6-trimethylcyclohexyl)-hex-1-yn-3-ol.

BACKGROUND OF THE INVENTION

In a copending application there is described a process for the preparation of compositions eminently consisting of trans-1-(2,6,6-trimethylcyclohexyl)-hexan-3-ol, a cycloaliphatic alcohol of formula

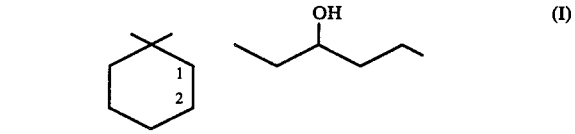

wherein the pecked line designates a C—C bond of trans configuration with respect to the methyl group in position 2 of the ring. By the said process, it is possible to prepare compositions consisting of from less than 100% to more than about 80% of trans-1-(2,6,6-trimethylcyclohexyl)-hexan-3-ol and a definite amount, but not more than about 20% of cis-1-(2,6,6-trimethylcyclohexyl)-hexan-3-ol. The cited copending application describes also the utilization of the obtained compositions as odorous active ingredients. The said invention was based upon the unexpected finding that trans-1-(2,6,6-trimethylcyclohexyl)-hexan-3-ol or mixtures thereof consisting essentially of said compound possess superior odorous properties than the prior known cis isomer [this compound is known in the art under the commercial name of TIMBEROL; origin Dragoco, Holzminden, FRG].

The instant invention provides an economic and advantageous process to prepare compositions enriched with the useful trans-1-(2,6,6-trimethylcyclohexyl)hexane-3-ol.

THE INVENTION

The process of the invention can be illustrated by the following reaction pathway:

Scheme

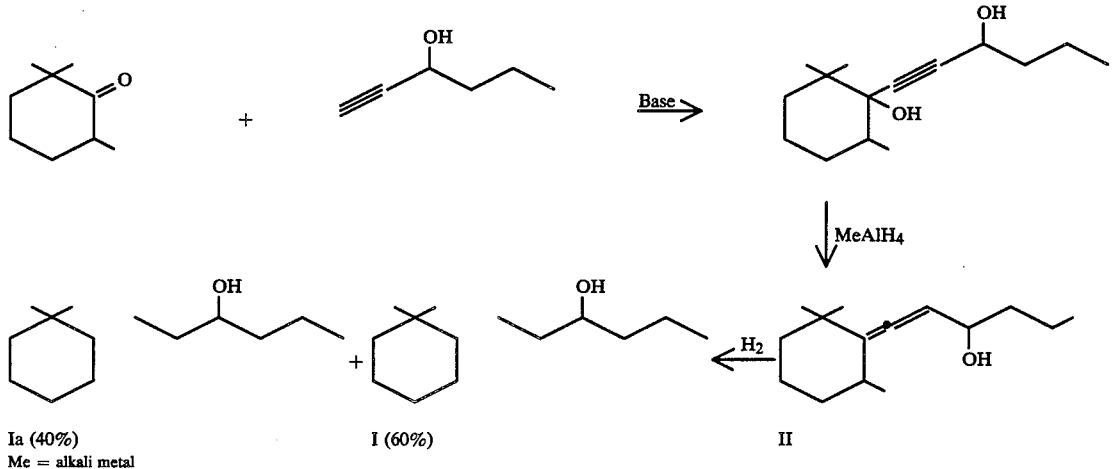

Ia (40%)  I (60%)  II
Me = alkali metal

The different steps of this process can be effected in a way analogous to those prior known. Thus the addition of hexynol to trimethylcyclohexanone can be carried out in the presence of a strong base by analogy with the method described by G. Ohloff et al. [Helv. Chim. Acta, 56, 1503 (1973)]. Suitable strong base include an alkali metal alkoxide or hydroxide, such as, e.g., potassium tertbutoxide, or sodium or potassium hydroxide.

The subsequent step, which consists in the reduction of the obtained diol, is carried out by means of an alkali metal aluminohydride, preferably of lithium aluminohydride. There is thus obtained an allenic carbinol which on catalytic hydrogenation, in the presence of Raney-nickel and copper chromite, give the desired product.

Such a hydrogenation is carried out in a way analogous to that described in DE-OS 24 55 761. The hydrogenation can thus take place at a temperature of between about 120° and 200° C., preferably at about 140°-150° C., and at a pressure of 20 to 100 atmospheres.

Said hydrogenation can be carried out also in the presence of $PtO_2$ as a catalyst in a medium constituted by acetic acid, and at room temperature and atmospheric pressure. In such a case, the desired end product was accompanied by 1-(2,6,6-trimethylcyclohexyl)-hexan-3-one and by 1-hexyl-2,6,6-trimethylcyclohexanone.

The composition directly obtained by the process of the invention which consists of a predominant amount, but not less than 60% by weight of trans-1-(2,6,6-trimethylcyclohexyl)-hexan-3-ol, and a definite amount, but not more than about 40% by weight of the corresponding cis isomer, is perfectly adapted to its use in perfumery. Consequently, a further purification of the obtained mixture to enhance its content of the more active trans isomer is superfluous.

The composition prepared in accordance with the process of the invention can be utilized to modify, improve or reinforce the fragrance properties of perfume compositions, perfume bases and concentrates, as well as the odor of a variety of articles such as cosmetics, soaps, shampoos, talcs, solid and liquid detergents, household materials, e.g. waxes, space deodorants or odorants.

As will be appreciated by those skilled in the art, the amount of the composition of the invention employed in a particular instance can vary over a relatively wide range, depending upon the odorous effect to be achieved. As usual in the art, the perfumer shall determine the best concentrations as a function of the product it is desired to perfume and of the nature of the coingredients he has chosen in a particular blend. The primary requirement is to obtain a well balanced overall olfactive effect of pleasant character.

Concentrations of the order of about 1% by weight of the composition of the invention based on the total weight of the composition into which it is added, can already achieve a pronounced effect. Of course, concentrations lower than the above given value can be employed to perfume articles such as e.g. soaps, cosmetics or detergents.

The active composition of the invention can be used either in its isolated form, or more frequently, in solution in the current solvents such as ethanol, anozol, or diethyl phthalate, or preferably in admixture with other usual perfume coingredients, supports or diluents.

The invention is better illustrated by the following examples wherein the temperature is indicated in degrees centigrade.

EXAMPLE 1 a. In a three-necked vessel of 250 ml equipped with a thermometer, a condenser and a dropping funnel, there were placed 23.9 g (0.427M) of finely ground KOH and 50 ml of anhydrous diethyl ether. 14 G (0.1M) of 2,6,6-trimethylcyclohexanone and 13.5 g (0.138M) of hex-1-yn-3-ol were then added dropwise to the obtained suspension. The addition is slightly exothermic. After standing for 24 h, the mixture was poured onto ice and extracted with ether while the combined extracts were washed with a 10% HCl solution, with brine until neutrality and finally dried over $Na_2SO_4$ and concentrated. A fractional distillation of the obtained residue gave 12 g of 1-(1-hydroxy-2,6,6-trimethylcyclohexyl)-hex-1-yn-3-ol having b.p. 100°-125°/13.3 Pa.

IR: 3400 $cm^{-1}$; NMR (60 MHz, $CDCl_3$): 0.98-1.18 (12H); 1.35-1.90 (11H); 4.45 (1H) δ ppm; MS: $M^+=238$; m/e: 184 (4), 155 (26), 141 (35), 127 (84), 109 (18), 95 (7), 85 (100), 69 (27), 57 (61), 43 (53).

b. A solution of 24.5 g (0.103M) of the diol, obtained according to the process described in paragraph a. above, in 50 ml of tetrahydrofuran (THF), was added dropwise under nitrogen to a suspension of 4.1 g (0.103M) of $LiAlH_4$ in 200 ml of anhydrous THF. The reaction is exothermic and the temperature of the reaction mixture raises to about 50°, whereupon the mixture was refluxed for 4 h, then it was kept stirring overnight at room temperature. After cooling, 4.1 ml of water, 4.1 ml of 15% aqueous NaOH and 12.3 ml of water were added to the reaction mixture and, after brief stirring, the mixture was filtered. On concentration of the clear filtrate, there was obtained a residue which upon distillation gave a fraction having b.p. 60°-74°/13.3 Pa (12.6 g) consisting of the desired allene.

IR: 3350, 1960 $cm^{-1}$; NMR (60 MHz, $CDCl_3$): 0.75-1.15 (12H); 1.25-1.83 (11H); 4.05 (1H); 5.2-5.45 (1H) δ ppm; MS: $M^+=222$; m/e: 205 (9), 189 (5), 180 (49), 161 (18), 150 (9), 135 (100), 121 (48), 107 (73), 93 (68), 81 (45), 69 (55), 55 (92), 43 (90), 41 (84), 29 (33).

c'. 10 G (0.045M) of the obtained allene, see paragraph b. above, were hydrogenated in 100 ml glacial acetic acid in the presence of 100 mg of $PtO_2$ at room temperature and atmospheric pressure. 2.57 L of hydrogen (0.115M) were thus absorbed.

After filtration, the reaction mixture was concentrated and the resulting residue distilled. 9.2 G of a colorless oil consisting of 67% of an isomeric mixture of about 60% of trans-1-(2,6,6-trimethylcyclohexyl)-hexan-3-ol and about 40% of cis-1-(2,6,6-trimethylcyclohexyl)-hexan-3-ol. A further purification was effected by bulb distillation (150°/13.3. Pa).

EXAMPLE 2

Two detergent powder bases were prepared by mixing the following ingredients (parts by weight):

|  | Composition | Comp. with Perborate |
|---|---|---|
| Linear sodium alkyl benzene sulfonate ($C_{11.5}$ chain length) | 8.0 | 6.4 |
| Ethoxylated tallow alcohol (14 EO) | 2.9 | 2.3 |
| Sodium soap (chain length $C_{12-16}$ 13-26%, $C_{18-22}$ 74-87%) | 3.5 | 2.8 |
| Sodium triphosphate | 43.8 | 35.0 |
| Sodium silicate | 7.5 | 6.0 |
| Magnesium silicate | 1.9 | 1.5 |
| Carboxymethylcellulose | 1.2 | 1.0 |
| Sodium EDTA | 0.2 | 0.2 |
| Sodium sulfate | 21.2 | 17.0 |
| Water | 9.8 | 7.8 |
| Sodium perborate | — | 20.0 |
|  | 100.0 | 100.0 |

By adding to a sample each of the above obtained detergent powders the product prepared in accordance with Example 1, there were obtained perfumed detergents with a distinct woody odor character.

What I claim is:

1. A process for the preparation of a composition containing not less than about 60% by weight of trans- 1-(2,6,6-trimethylcyclohexyl)-hexan-3-ol and not more than about 40% by weight of cis-1-(2,6,6-trimethylcyclohexyl)-hexan-3-ol, which comprises the following sequential steps:
   a. the addition of hex-1-yn-3-ol to 2,6,6-trimethylcyclohexanone in the presence of an alkali metal alkoxide or hydroxide to give 1-(1-hydroxy-2,6,6-trimethylcyclohexyl)-hex-1-yn-3-ol;
   b. the reduction of said hexynol by means of an alkali metal aluminohydride to give an allenic carbinol of formula

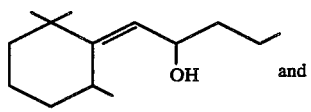
(II)

and c. the catalytic hydrogenation of said carbinol wherein hydrogen is added at a pressure higher than the atmospheric pressure and in the presence of Raney-nickel and copper chromite.

2. The process of claim 1, wherein the alkali metal aluminohydride is LiAlH₄.

3. A process for the preparation of a composition containing not less than about 60% by weight of trans-1-(2,6,6-trimethylcyclohexyl)-hexan-3-ol and not more than about 40% by weight of cis-1-(2,6,6-trimethylcyclohexyl)-hexan-3-ol, which comprises the following sequential steps:
   a. the addition of hex-1-yn-3-ol to 2,6,6-trimethylcyclohexanone in the presence of an alkali metal alkoxide or hydroxide to give 1-(1-hydroxy-2,6,6-trimethylcyclohexyl)-hex-1-yn-3-ol;
   b. the reduction of said hexynol by means of an alkali metal aluminohydride to give an allenic carbinol of formula

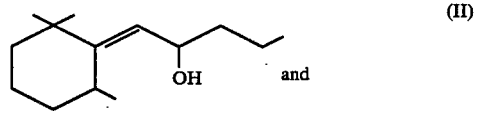
(II)

and c. the catalytic hydrogenation of said carbinol wherein hydrogen is added at room temperature and atmospheric pressure in the presence of PtO₂.

4. The process of claim 3 wherein the alkali metal aluminohydride is LiAlH₄.

* * * * *

UNITED STATES PATENT AND TRADEMARK OFFICE
CERTIFICATE OF CORRECTION

PATENT NO. : 4,588,849

DATED : May 13, 1986

INVENTOR(S) : Karl-Heinrich Schulte-Elte

It is certified that error appears in the above-identified patent and that said Letters Patent is hereby corrected as shown below:

Formula (I), column 2, lines 1-8,

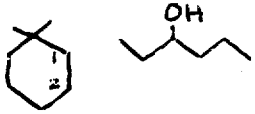

should be --

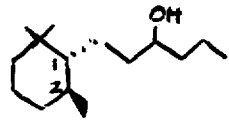

Formula Ia, column 1, lines 33-55,

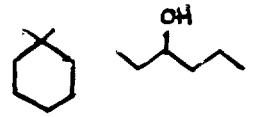

should be --

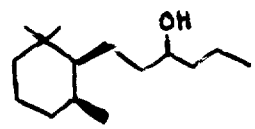

UNITED STATES PATENT AND TRADEMARK OFFICE
CERTIFICATE OF CORRECTION

PATENT NO. : 4,588,849

DATED : May 13, 1986

INVENTOR(S) : Karl-Heinrich Schulte-Elte

It is certified that error appears in the above-identified patent and that said Letters Patent is hereby corrected as shown below:

Formula I, column 1, lines 33-55,

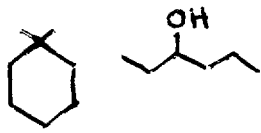

should be --

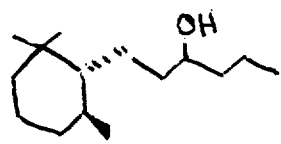

Signed and Sealed this

Fourteenth Day of October, 1986

[SEAL]

*Attest:*

DONALD J. QUIGG

*Attesting Officer*  *Commissioner of Patents and Trademarks*